United States Patent
Jadhav et al.

(10) Patent No.: US 10,881,445 B2
(45) Date of Patent: Jan. 5, 2021

(54) ADAPTERS, SYSTEMS INCORPORATING THE SAME, AND METHODS FOR PROVIDING AN ELECTROSURGICAL FORCEPS WITH CLIP-APPLYING FUNCTIONALITY

(71) Applicant: COVIDIEN LP, Mansfield, MA (US)

(72) Inventors: Amarsinh D. Jadhav, Karnataka (IN); Yogesh K. Vikharankar, Maharashtra (IN)

(73) Assignee: Covidien LP, Mansfield, MA (US)

( * ) Notice: Subject to any disclaimer, the term of this patent is extended or adjusted under 35 U.S.C. 154(b) by 1003 days.

(21) Appl. No.: 15/428,609

(22) Filed: Feb. 9, 2017

(65) Prior Publication Data

US 2018/0221023 A1    Aug. 9, 2018

(51) Int. Cl.
*A61B 17/122*   (2006.01)
*A61B 18/08*   (2006.01)
(Continued)

(52) U.S. Cl.
CPC .......... *A61B 18/085* (2013.01); *A61B 17/122* (2013.01); *A61B 17/1285* (2013.01);
(Continued)

(58) Field of Classification Search
CPC . A61B 17/122; A61B 17/1285; A61B 17/285; A61B 17/295; A61B 2017/00017;
(Continued)

(56) References Cited

U.S. PATENT DOCUMENTS

D249,549 S    9/1978 Pike
4,294,355 A    10/1981 Jewusiak et al.
(Continued)

FOREIGN PATENT DOCUMENTS

CN    201299462    9/2009
DE    2415263 A1    10/1975
(Continued)

OTHER PUBLICATIONS

Extended European Search Report issued in corresponding EP Application No. 18155801.6 dated Sep. 19, 2018, 13 pages.
(Continued)

*Primary Examiner* — Michael F Peffley
*Assistant Examiner* — Khadijeh A Vahdat
(74) *Attorney, Agent, or Firm* — Carter, DeLuca & Farrell LLP

(57) ABSTRACT

Adapters for use with surgical systems including a surgical forceps, and a surgical clip; and methods for providing clip-applying functionality are disclosed. The adapter is releasably engagable with the end effector assembly of the surgical forceps. The surgical clip is releasably engagable with the adapter. With the surgical clip engaged with the adapter and the adapter engaged with the end effector assembly, the jaw members of the end effector assembly are configured to move from the spaced-apart position towards the approximated position to move the jaw bodies of the adapter towards one another to, in turn, urge the legs of the surgical clip towards one another to form the surgical clip.

10 Claims, 6 Drawing Sheets

(51) Int. Cl.
- *A61B 18/14* (2006.01)
- *A61B 17/128* (2006.01)
- *A61B 34/30* (2016.01)
- *A61B 17/00* (2006.01)
- *A61B 18/00* (2006.01)
- *A61B 17/295* (2006.01)
- *A61B 17/29* (2006.01)
- *A61B 17/28* (2006.01)
- *A61B 17/285* (2006.01)
- *A61B 90/00* (2016.01)

(52) U.S. Cl.
CPC ........ *A61B 18/1445* (2013.01); *A61B 17/285* (2013.01); *A61B 17/295* (2013.01); *A61B 18/1402* (2013.01); *A61B 34/30* (2016.02); *A61B 2017/00017* (2013.01); *A61B 2017/00353* (2013.01); *A61B 2017/00477* (2013.01); *A61B 2017/2825* (2013.01); *A61B 2017/2829* (2013.01); *A61B 2017/2931* (2013.01); *A61B 2018/0063* (2013.01); *A61B 2018/00172* (2013.01); *A61B 2018/00196* (2013.01); *A61B 2018/00202* (2013.01); *A61B 2018/00428* (2013.01); *A61B 2018/00607* (2013.01); *A61B 2018/00702* (2013.01); *A61B 2018/1455* (2013.01); *A61B 2090/0808* (2016.02)

(58) Field of Classification Search
CPC ........... A61B 2017/00353; A61B 2017/00477; A61B 2017/2825; A61B 2017/2829; A61B 2017/2931; A61B 18/085; A61B 18/14; A61B 18/1402; A61B 18/1445; A61B 2018/00172; A61B 2018/00196; A61B 2018/00202; A61B 2018/00428; A61B 2018/00607; A61B 2018/0063; A61B 2018/00702; A61B 2018/1455; A61B 2090/0808; A61B 34/30; A61B 5/6838; A61B 5/6884; A61B 17/0487; A61B 17/08; A61B 17/083; A61B 2017/00584; A61B 2017/0488; A61B 2017/049; A61B 2017/1225
USPC .............................. 606/51–52, 169, 205–207
See application file for complete search history.

(56) References Cited

U.S. PATENT DOCUMENTS

| | | | |
|---|---|---|---|
| D263,020 S | 2/1982 | Rau, III | |
| 4,361,229 A | 11/1982 | Mericle | |
| 4,509,518 A * | 4/1985 | McGarry | A61B 17/128 606/143 |
| 4,570,633 A | 2/1986 | Golden | |
| D295,893 S | 5/1988 | Sharkany et al. | |
| D295,894 S | 5/1988 | Sharkany et al. | |
| D298,353 S | 11/1988 | Manno | |
| D299,413 S | 1/1989 | DeCarolis | |
| 5,026,379 A | 6/1991 | Yoon | |
| 5,201,900 A * | 4/1993 | Nardella | A61B 17/122 227/902 |
| D343,453 S | 1/1994 | Noda | |
| D348,930 S | 7/1994 | Olson | |
| D349,341 S | 8/1994 | Lichtman et al. | |
| D354,564 S | 1/1995 | Medema | |
| D358,887 S | 5/1995 | Feinberg | |
| D384,413 S | 9/1997 | Zlock et al. | |
| H1745 H | 8/1998 | Paraschac | |
| D402,028 S | 12/1998 | Grimm et al. | |
| D408,018 S | 4/1999 | McNaughton | |
| D416,089 S | 11/1999 | Barton et al. | |
| D424,694 S | 5/2000 | Tetzlaff et al. | |
| D425,201 S | 5/2000 | Tetzlaff et al. | |
| H1904 H | 10/2000 | Yates et al. | |
| D449,886 S | 10/2001 | Tetzlaff et al. | |
| D453,923 S | 2/2002 | Olson | |
| D454,951 S | 3/2002 | Bon | |
| D457,958 S | 5/2002 | Dycus et al. | |
| D457,959 S | 5/2002 | Tetzlaff et al. | |
| H2037 H | 7/2002 | Yates et al. | |
| D465,281 S | 11/2002 | Lang | |
| D466,209 S | 11/2002 | Bon | |
| D493,888 S | 8/2004 | Reschke | |
| D496,997 S | 10/2004 | Dycus et al. | |
| D499,181 S | 11/2004 | Dycus et al. | |
| D502,994 S | 3/2005 | Blake, III | |
| D509,297 S | 9/2005 | Wells | |
| D525,361 S | 7/2006 | Hushka | |
| D531,311 S | 10/2006 | Guerra et al. | |
| D533,274 S | 12/2006 | Visconti et al. | |
| D533,942 S | 12/2006 | Kerr et al. | |
| D535,027 S | 1/2007 | James et al. | |
| D538,932 S | 3/2007 | Malik | |
| D541,418 S | 4/2007 | Schechter et al. | |
| D541,611 S | 5/2007 | Aglassinger | |
| D541,938 S | 5/2007 | Kerr et al. | |
| D545,432 S | 6/2007 | Watanabe | |
| D547,154 S | 7/2007 | Lee | |
| D564,662 S | 3/2008 | Moses et al. | |
| D567,943 S | 4/2008 | Moses et al. | |
| D575,395 S | 8/2008 | Hushka | |
| D575,401 S | 8/2008 | Hixson et al. | |
| D582,038 S | 12/2008 | Swoyer et al. | |
| D617,900 S | 6/2010 | Kingsley et al. | |
| D617,901 S | 6/2010 | Unger et al. | |
| D617,902 S | 6/2010 | Twomey et al. | |
| D617,903 S | 6/2010 | Unger et al. | |
| D618,798 S | 6/2010 | Olson et al. | |
| D621,503 S | 8/2010 | Otten et al. | |
| D627,462 S | 11/2010 | Kingsley | |
| D628,289 S | 11/2010 | Romero | |
| D628,290 S | 11/2010 | Romero | |
| D630,324 S | 1/2011 | Reschke | |
| 7,875,029 B1 | 1/2011 | Hausen | |
| D649,249 S | 11/2011 | Guerra | |
| D649,643 S | 11/2011 | Allen, IV et al. | |
| D661,394 S | 6/2012 | Romero et al. | |
| D670,808 S | 11/2012 | Moua et al. | |
| D680,220 S | 4/2013 | Rachlin | |
| 8,444,664 B2 | 5/2013 | Balanev et al. | |
| 9,084,608 B2 | 7/2015 | Larson et al. | |
| 9,211,657 B2 | 12/2015 | Ackley et al. | |
| 2008/0147092 A1 | 6/2008 | Rogge et al. | |
| 2008/0243141 A1 | 10/2008 | Privitera et al. | |
| 2012/0083786 A1 | 4/2012 | Artale et al. | |
| 2013/0046303 A1 | 2/2013 | Evans et al. | |
| 2013/0255063 A1 | 10/2013 | Hart et al. | |
| 2014/0221995 A1 | 8/2014 | Guerra et al. | |
| 2014/0221999 A1 | 8/2014 | Cunningham et al. | |
| 2014/0228842 A1 | 8/2014 | Dycus et al. | |
| 2014/0230243 A1 | 8/2014 | Roy et al. | |
| 2014/0236149 A1 | 8/2014 | Kharin et al. | |
| 2014/0243811 A1 | 8/2014 | Reschke et al. | |
| 2014/0243824 A1 | 8/2014 | Gilbert | |
| 2014/0249528 A1 | 9/2014 | Hixson et al. | |
| 2014/0250686 A1 | 9/2014 | Hempstead et al. | |
| 2014/0257274 A1 | 9/2014 | McCullough, Jr. et al. | |
| 2014/0257283 A1 | 9/2014 | Johnson et al. | |
| 2014/0257284 A1 | 9/2014 | Artale | |
| 2014/0257285 A1 | 9/2014 | Moua | |
| 2014/0276803 A1 | 9/2014 | Hart | |
| 2014/0284313 A1 | 9/2014 | Allen, IV et al. | |
| 2014/0288549 A1 | 9/2014 | McKenna et al. | |
| 2014/0288553 A1 | 9/2014 | Johnson et al. | |
| 2014/0330308 A1 | 11/2014 | Hart et al. | |
| 2014/0336635 A1 | 11/2014 | Hart et al. | |
| 2014/0353188 A1 | 12/2014 | Reschke et al. | |
| 2015/0018816 A1 | 1/2015 | Latimer | |
| 2015/0025528 A1 | 1/2015 | Arts | |
| 2015/0032106 A1 | 1/2015 | Rachlin | |

(56) References Cited

U.S. PATENT DOCUMENTS

| | | |
|---|---|---|
| 2015/0051598 A1 | 2/2015 | Orszulak et al. |
| 2015/0051640 A1 | 2/2015 | Twomey et al. |
| 2015/0066026 A1 | 3/2015 | Hart et al. |
| 2015/0080880 A1 | 3/2015 | Sartor et al. |
| 2015/0080889 A1 | 3/2015 | Cunningham et al. |
| 2015/0082928 A1 | 3/2015 | Kappus et al. |
| 2015/0088122 A1 | 3/2015 | Jensen |
| 2015/0088126 A1 | 3/2015 | Duffin et al. |
| 2015/0088128 A1 | 3/2015 | Couture |
| 2015/0094714 A1 | 4/2015 | Lee et al. |
| 2015/0282867 A1* | 10/2015 | Keller ................ A61B 18/1445 606/52 |
| 2016/0367239 A1 | 12/2016 | Mumaw et al. |

FOREIGN PATENT DOCUMENTS

| | | |
|---|---|---|
| DE | 02514501 A1 | 10/1976 |
| DE | 2627679 A1 | 1/1977 |
| DE | 03423356 C2 | 6/1986 |
| DE | 03612646 A1 | 4/1987 |
| DE | 3627221 A1 | 2/1988 |
| DE | 8712328 U1 | 2/1988 |
| DE | 04303882 C2 | 2/1995 |
| DE | 04403252 A1 | 8/1995 |
| DE | 19515914 C1 | 7/1996 |
| DE | 19506363 A1 | 8/1996 |
| DE | 29616210 U1 | 11/1996 |
| DE | 19608716 C1 | 4/1997 |
| DE | 19751106 A1 | 5/1998 |
| DE | 19751108 A1 | 5/1999 |
| DE | 19946527 C1 | 7/2001 |
| DE | 20121161 U1 | 4/2002 |
| DE | 10045375 C2 | 10/2002 |
| DE | 202007009165 U1 | 8/2007 |
| DE | 202007009317 U1 | 8/2007 |
| DE | 202007009318 U1 | 8/2007 |
| DE | 10031773 B4 | 11/2007 |
| DE | 202007016233 U1 | 1/2008 |
| DE | 19738457 B4 | 1/2009 |
| DE | 102004026179 B4 | 1/2009 |
| DE | 102008018406 B3 | 7/2009 |
| EP | 1281878 A1 | 2/2003 |
| EP | 1159926 A3 | 3/2003 |
| EP | 2926754 A2 | 10/2015 |
| JP | 61-501068 | 9/1984 |
| JP | 10-24051 A | 1/1989 |
| JP | 11-47150 A | 6/1989 |
| JP | 6-502328 | 3/1992 |
| JP | 5-5106 | 1/1993 |
| JP | 05-40112 | 2/1993 |
| JP | 0006030945 A | 2/1994 |
| JP | 6-121797 A | 5/1994 |
| JP | 6-285078 A | 10/1994 |
| JP | 6-511401 | 12/1994 |
| JP | 06343644 A | 12/1994 |
| JP | 07265328 A | 10/1995 |
| JP | 8-56955 | 5/1996 |
| JP | 08252263 A | 10/1996 |
| JP | 8-289895 A | 11/1996 |
| JP | 8-317934 A | 12/1996 |
| JP | 8-317936 A | 12/1996 |
| JP | 9-10223 C | 1/1997 |
| JP | 09000538 A | 1/1997 |
| JP | 9-122138 A | 5/1997 |
| JP | 0010000195 A | 1/1998 |
| JP | 10-155798 A | 6/1998 |
| JP | 11-47149 | 2/1999 |
| JP | 11-070124 A | 3/1999 |
| JP | 11-169381 A | 6/1999 |
| JP | 11-192238 A | 7/1999 |
| JP | 11244298 A | 9/1999 |
| JP | 2000-102545 A | 4/2000 |
| JP | 2000-135222 A | 5/2000 |
| JP | 2000342599 A | 12/2000 |
| JP | 2000350732 A | 12/2000 |
| JP | 2001008944 A | 1/2001 |
| JP | 2001-29355 | 2/2001 |
| JP | 2001029356 A | 2/2001 |
| JP | 2001-03400 | 4/2001 |
| JP | 2001128990 A | 5/2001 |
| JP | 2001-190564 A | 7/2001 |
| JP | 2002-136525 A | 5/2002 |
| JP | 2002-528166 A | 9/2002 |
| JP | 2003-116871 A | 4/2003 |
| JP | 2003-175052 A | 6/2003 |
| JP | 2003245285 A | 9/2003 |
| JP | 2004-517668 A | 6/2004 |
| JP | 2004-528869 A | 9/2004 |
| JP | 2005-152663 A | 6/2005 |
| JP | 2005-253789 A | 9/2005 |
| JP | 2005312807 A | 11/2005 |
| JP | 2006-015078 A | 1/2006 |
| JP | 2006-501939 A | 1/2006 |
| JP | 2006-095316 A | 4/2006 |
| JP | 2008-054926 A | 3/2008 |
| JP | 2011125195 A | 6/2011 |
| SU | 401367 A1 | 11/1974 |
| WO | 9424949 A1 | 11/1994 |
| WO | 0036986 A1 | 6/2000 |
| WO | 0059392 A1 | 10/2000 |
| WO | 0115614 A1 | 3/2001 |
| WO | 0154604 A1 | 8/2001 |
| WO | 02/45589 | 6/2002 |
| WO | 06/021269 A1 | 3/2006 |
| WO | 05110264 A3 | 4/2006 |
| WO | 08/040483 A1 | 4/2008 |
| WO | 2011/018154 A1 | 2/2011 |

OTHER PUBLICATIONS

Partial European Search report issued in corresponding EP application No. 18155801.6 dated May 16, 2018.
Heniford et al. "Initial Research and Clinical Results with an Electrothermal Bipolar Vessel Sealer" Oct. 1999. (1 page).
Michael Choti, "Abdominoperineal Resection with the LigaSure Vessel Sealing System and LigaSure Atlas 20 cm Open Instrument"; Innovations That Work, Jun. 2003. (4 pages).
Chung et al., "Clinical Experience of Sutureless Closed Hemorrhoidectomy with LigaSure" Diseases of the Colon & Rectum vol. 46, No. 1 Jan. 2003, pp. 87-92.
Tinkcler L.F., "Combined Diathermy and Suction Forceps", Feb. 6, 1967 (Feb. 6, 1965), British Medical Journal Feb. 6, 1976, vol. 1, nr. 5431 p. 361, ISSN: 0007-1447.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC; Date: Aug. 2003. (1 page).
Peterson et al. "Comparison of Healing Process Following Ligation with Sutures and Bipolar Vessel Sealing" Surgical Technology International (2001). (8 pages).
"Electrosurgery: A Historical Overview" Innovations in Electrosurgery; Sales/Product Literature; Dec. 31, 2000. (6 pages).
Johnson et al. "Evaluation of a Bipolar Electrothermal Vessel Sealing Device in Hemorrhoidectomy" Sales/Product Literature; Jan. 2004. (1 page).
E. David Crawford "Evaluation of a New Vessel Sealing Device in Urologic Cancer Surgery" Sales/Product Literature 2000. (1 page).
Johnson et al. "Evaluation of the LigaSure Vessel Sealing System in Hemorrhoidectormy" American College of Surgeons (ACS) Clinicla Congress Poster (2000). (1 page).
Muller et al., "Extended Left Hemicolectomy Using the LigaSure Vessel Sealing System" Innovations That Work, Sep. 1999. (4 pages).
Kennedy et al. "High-burst-strength, feedback-controlled bipolar vessel sealing" Surgical Endoscopy (1998) 12:876-878.
Burdette et al. "In Vivo Probe Measurement Technique for Determining Dielectric Properties at VHF Through Microwave Frequen-

(56) References Cited

OTHER PUBLICATIONS cies", IEEE Transactions on Microwave Theory and Techniques, vol. MTT-28, No. 4, Apr. 1980 pp. 414-427.

Carus et al., "Initial Experience With the LigaSure Vessel Sealing System in Abdominal Surgery" Innovations That Work, Jun. 2002. (4 pages).

Heniford et al. "Initial Results with an Electrothermal Bipolar Vessel Sealer" Surgical Endoscopy (2000) 15:799-801. (4 pages).

Herman et al., "Laparoscopic Intestinal Resection With the LigaSure Vessel Sealing System: A Case Report"; Innovations That Work, Feb. 2002. (4 pages).

Koyle et al., "Laparoscopic Palomo Varicocele Ligation in Children and Adolescents" Pediatric Endosurgery & Innovative Techniques, vol. 6, No. 1, 2002, pp. 15-19.

W. Scott Helton, "LigaSure Vessel Sealing System: Revolutionary Hemostasis Product for General Surgery"; Sales/Product Literature 1999. (1 page).

LigaSure Vessel Sealing System, the Seal of Confidence in General, Gynecologic, Urologic, and Laparaoscopic Surgery; Sales/Product Literature; Apr. 2002. (8 pages).

Joseph Ortenberg "LigaSure System Used in Laparoscopic 1st and 2nd Stage Orchiopexy" Innovations That Work, Nov. 2002. (4 pages).

Sigel et al. "The Mechanism of Blood Vessel Closure by High Frequency Electrocoagulation" Surgery Gynecology & Obstetrics, Oct. 1965 pp. 823-831.

Sampayan et al, "Multilayer Ultra-High Gradient Insulator Technology" Discharges and Electrical Insulation in Vacuum, 1998. Netherlands Aug. 17-21, 1998; vol. 2, pp. 740-743.

Paul G. Horgan, "A Novel Technique for Parenchymal Division During Hepatectomy" The American Journal of Surgery, vol. 181, No. 3, Apr. 2001 pp. 236-237.

Benaron et al., "Optical Time-Of-Flight and Absorbance Imaging of Biologic Media", Science, American Association for the Advancement of Science, Washington, DC, vol. 259, Mar. 5, 1993, pp. 1463-1466.

Olsson et al. "Radical Cystectomy in Females" Current Surgical Techniques in Urology, vol. 14, Issue 3, 2001. (8 pages).

Palazzo et al. "Randomized clinical trial of Ligasure versus open haemorrhoidectomy" British Journal of Surgery 2002, 39, 154-157.

Levy et al. "Randomized Trial of Suture Versus Electrosurgical Bipolar Vessel Sealing in Vaginal hysterectomy" Obstetrics & Gynecology, vol. 102, No. 1, Jul. 2003, pp. 147-151.

"Reducing Needlestick Injuries in the Operating Room" Sales/Product Literature 2001. (1 page).

Bergdahl et al. "Studies on Coagulation and the Development of an Automatic Computerized Bipolar Coagulator" J. Neurosurg, vol. 75, Jul. 1991, pp. 148-151.

Strasberg et al. "A Phase I Study of the LigaSure Vessel Sealing System in Hepatic Surgery" Section of HPB Surger, Washington University School of Medicine, St. Louis MO, Presented at AHPBA, Feb. 2001. (1 page).

Seyfan et al. "Sutureless Closed Hemorrhoidectomy: A New Technique" Annals of Surgery vol. 234 No. 1, Jul. 2001 pp. 21-24.

Levy et al., "Update on Hysterectomy—New Technologies and Techniques" OBG Management, Feb. 2003. (15 pages).

Dulemba et al. "Use of a Bipolar Electrothermal Vessel Sealer in Laparoscopically Assisted Vaginal Hysterectomy" Sales/Product Literature; Jan. 2004. (1 page).

Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.

Sengupta et al., "Use of a Computer-Controlled Bipolar Diathermy System in Radical Prostatectomies and Other Open Urological Surgery" ANZ Journal of Surgery (2001) 71.9 pp. 538-540.

Rothenberg et al. "Use of the LigaSure Vessel Sealing System in Minimally Invasive Surgery in Children" Int'l Pediatric Endosurgery Group (IPEG) 2000. (1 page).

Crawford et al. "Use of the LigaSure Vessel Sealing System in Urologic Cancer Surgery" Grand Rounds in Urology 1999 vol. 1 Issue 4 pp. 10-17.

Craig Johnson, "Use of the LigaSure Vessel Sealing System in Bloodless Hemorrhoidectomy" Innovations That Work, Mar. 2000. (4 pages).

Levy et al. "Use of a New Energy-based Vessel Ligation Device During Vaginal Hysterectomy" Int'l Federation of Gynecology and Obstetrics (FIGO) World Congress 1999. (1 page).

Barbara Levy, "Use of a New Vessel Ligation Device During Vaginal Hysterectomy" FIGO 2000, Washington, D.C.. (1 page).

E. David Crawford "Use of a Novel Vessel Sealing Technology in Management of the Dorsal Veinous Complex" Sales/Product Literature 2000. (1 page).

Jarrett et al., "Use of the LigaSure Vessel Sealing System for Peri-Hilar Vessels in Laparoscopic Nephrectomy" Sales/Product Literature 2000. (1 page).

Crouch et al. "A Velocity-Dependent Model for Needle Insertion in Soft Tissue" MICCAI 2005; LNCS 3750 pp. 624-632, Dated: 2005.

McLellan et al. "Vessel Sealing for Hemostasis During Pelvic Surgery" Int'l Federation of Gynecology and Obstetrics FIGO World Congress 2000, Washington, D.C.. (1 page).

McLellan et al. "Vessel Sealing for Hemostasis During Gynecologic Surgery" Sales/Product Literature 1999. (1 page).

U.S. Appl. No. 08/926,869, filed Sep. 10, 1997; inventor: James G. Chandler, Abandoned.

U.S. Appl. No. 09/177,950, filed Oct. 23, 1998; inventor: Randel A. Frazier, abandoned.

U.S. Appl. No. 09/387,883, filed Sep. 1, 1999; inventor: Dale F. Schmaltz, abandoned.

U.S. Appl. No. 09/591,328, filed Jun. 9, 2000; inventor: Thomas P. Ryan, abandoned.

U.S. Appl. No. 12/336,970, filed Dec. 17, 2008; inventor: Paul R. Sremcich, abandoned.

U.S. Appl. No. 14/065,644, filed Oct. 29, 2013; inventor: Reschke, abandoned.

* cited by examiner

ADAPTERS, SYSTEMS INCORPORATING THE SAME, AND METHODS FOR PROVIDING AN ELECTROSURGICAL FORCEPS WITH CLIP-APPLYING FUNCTIONALITY

BACKGROUND

1. Technical Field

The present disclosure relates generally to the field of surgical instruments. In particular, the present disclosure relates to adapters, systems incorporating the same, and methods for providing an electrosurgical forceps with clip-applying functionality.

2. Background of Related Art

Electrosurgical forceps utilize both mechanical clamping action and electrical energy to effect hemostasis by heating tissue to treat, e.g., coagulate, cauterize, and/or seal, tissue. Typically, once tissue is treated, the surgeon has to accurately sever the treated tissue. Accordingly, many forceps have been designed which incorporate a knife that effectively severs tissue after treatment thereof.

Surgical clip appliers are utilized to form a surgical clip over a blood vessel or other duct. During the course of a surgical procedure, it may be necessary for the surgeon to form a surgical clip about a blood vessel or other duct to terminate the flow of body fluids therethrough.

In some surgical procedures, it may be necessary to treat tissue using energy and, further, cut the treated tissue, e.g., using an electrosurgical forceps, and to terminate the flow of fluid through a blood vessel or other duct, e.g., using a surgical clip.

SUMMARY

As used herein, the term "distal" refers to the portion that is being described which is further from a user, while the term "proximal" refers to the portion that is being described which is closer to a user. Further, to the extent consistent, any of the aspects described herein may be used in conjunction with any or all of the other aspects described herein.

Provided in accordance with aspects of the present disclosure is a surgical system including a surgical forceps, an adapter, and a surgical clip. The surgical forceps includes an end effector assembly including a pair of jaw members each defining a tissue-contacting surface. The jaw members are movable from a spaced-apart position to an approximated position.

The adapter is releasably engagable with the end effector assembly. The adapter includes a pair of jaw bodies and an interconnect band coupling the jaw bodies with one another. Each jaw body includes a support plate configured for positioning on the tissue-contacting surface of one of the jaw members, and a chuck.

The surgical clip is releasably engagable with the adapter. The surgical clip includes a pair of legs and a backspan interconnecting the legs. Each leg is configured for receipt at least partially within the chuck of one of the jaw bodies of the adapter. With the surgical clip engaged with the adapter and the adapter engaged with the end effector assembly, the jaw members are configured to move from the spaced-apart position towards the approximated position to move the jaw bodies towards one another to, in turn, urge the legs of the surgical clip towards one another to form the surgical clip.

In an aspect of the present disclosure, the forceps includes a knife that is selectively translatable relative to the jaw members between a retracted position and an extended position, wherein the knife extends at least partially through a knife channel defined within at least one of the tissue-contacting surfaces, and wherein the at least one of the jaw bodies of the adapter includes a fin configured for receipt within the knife channel of one of the jaw members.

In an aspect of the present disclosure, either or both of the tissue contacting surfaces are adapted to connect to a source of electrosurgical energy.

In another aspect of the present disclosure, the chuck of each jaw body defines a channel configured to receive a portion of one of the legs of the surgical clip therein.

In another aspect of the present disclosure, the chuck of each jaw body defines at least one location feature. Each leg of the surgical clip defines at least one complementary location feature configured to engage the at least one location feature to facilitate alignment of the surgical clip relative to the adapter.

In still another aspect of the present disclosure, the at least one location feature is at least one recess and the at least one complementary location feature is at least one knob configured for engagement within the at least one recess.

In yet another aspect of the present disclosure, the chuck of each jaw body includes a pair of spaced-apart feet configured to receive a portion of the surgical clip therebetween. In such aspects, each foot defines one of the at least one location features.

In still yet another aspect of the present disclosure, the adapter is configured to engage the end effector assembly in a pre-compressed position. More specifically, the adapter may define an at-rest position, wherein the interconnect band defines a first radius of curvature, and, when the adapter is engaged with the end effector assembly, the adapter is retained in the pre-compressed position wherein the interconnect band is flexed to define a second radius of curvature smaller than the first radius of curvature.

In another aspect of the present disclosure, the surgical clip is configured to engage the adapter in a pre-compressed position. More specifically, the surgical clip may define an initial condition, wherein the backspan defines a first radius of curvature, and, when the surgical clip is engaged with the adapter, the surgical clip is retained in the pre-compressed condition wherein the backspan is flexed to define a second radius of curvature smaller than the first radius of curvature.

An adapter provided in accordance with aspects of the present disclosure and configured for use with a surgical instrument to provide clip-applying functionality thereto includes a pair of jaw bodies and an interconnect band. Each jaw body includes a support plate, a fin, and a chuck. The support plate defines an inwardly-facing side, an outwardly-facing side, a proximal end portion, and a distal end portion. The fin extends longitudinally along a portion of the outwardly-facing side of the support plate. The chuck is disposed on the inwardly-facing side of the support plate and defines a channel and at least one location feature. The interconnect band extends between and couples the proximal end portions of the support plates of the jaw bodies with one another. The interconnect band is configured to flex from an at-rest position, corresponding to a further-spaced position of the jaw bodies, to a flexed position, corresponding to a closer-approximated position of the jaw members. With legs of a surgical clip received with the channels of the chucks and complementary location features of the legs of the surgical clip received within the at least one location feature of each of the chucks, movement of the jaw bodies from the further-spaced position towards the closer-approximated position moves the legs of the surgical clip from an initial condition towards a formed condition.

In an aspect of the present disclosure, the jaw bodies and the interconnect band are a monolithic component.

In another aspect of the present disclosure, the chucks are disposed towards the distal end portions of the support plates such that a proximal portion of an inwardly-facing surface of each of the support plates is exposed.

In yet another aspect of the present disclosure, the fins extend from the proximal end portions of the support plates to points proximal of the distal end portions of the support plates.

In still another aspect of the present disclosure, each chuck includes a pair of spaced-apart feet. Each foot defines one of the at least one location features therein.

A method of surgery provided in accordance with aspects of the present disclosure includes moving a pair of jaw members from a spaced-apart position to an approximated position to grasp tissue between tissue-contacting surfaces of the jaw members. The method further includes conducting electrosurgical energy between the tissue-contacting surfaces to treat tissue grasped therebetween and/or translating a knife through knife channels defined within the tissue-contacting surfaces to cut tissue grasped between the tissue-contacting surfaces. The method additionally includes operably engaging an adapter with the jaw members such that a first portion of the adapter is disposed on each of the tissue-contacting surfaces, engaging a surgical clip with the adapter, and moving the pair of jaw members from the spaced-apart position towards the approximated position to form the surgical clip about tissue.

In an aspect of the present disclosure, the surgical clip is engaged with the adapter prior to operably engaging the adapter with the jaw members. Alternatively, the surgical clip may be engaged with the adapter subsequent to operably engaging the adapter with the jaw members.

In an aspect of the present disclosure, operably engaging the adapter includes inserting a second portion of the adapter into each of the knife channels and such that the first portion of the adapter is disposed on each of the tissue-contacting surfaces.

In another aspect of the present disclosure, the method further includes returning the pair of jaw members to the spaced-apart position, engaging a second surgical clip with the adapter, and moving the pair of jaw members from the spaced-apart position towards the approximated position to form the second surgical clip about tissue.

BRIEF DESCRIPTION OF THE DRAWINGS

Various aspects and features of the present disclosure are described hereinbelow with reference to the drawings wherein like numerals designate identical or corresponding elements in each of the several views.

DETAILED DESCRIPTION

The present disclosure relates to adapters, systems incorporating such adapters, and methods for providing electrosurgical forceps with clip-applying functionality. Although particular electrosurgical forceps are detailed herein, it is contemplated that the adapters of the present disclosure be likewise configured for use with other suitable electrosurgical forceps and/or other surgical instruments, and that the present disclosure also encompasses systems including the presently-disclosed adapters and such instruments.

Figure 1:
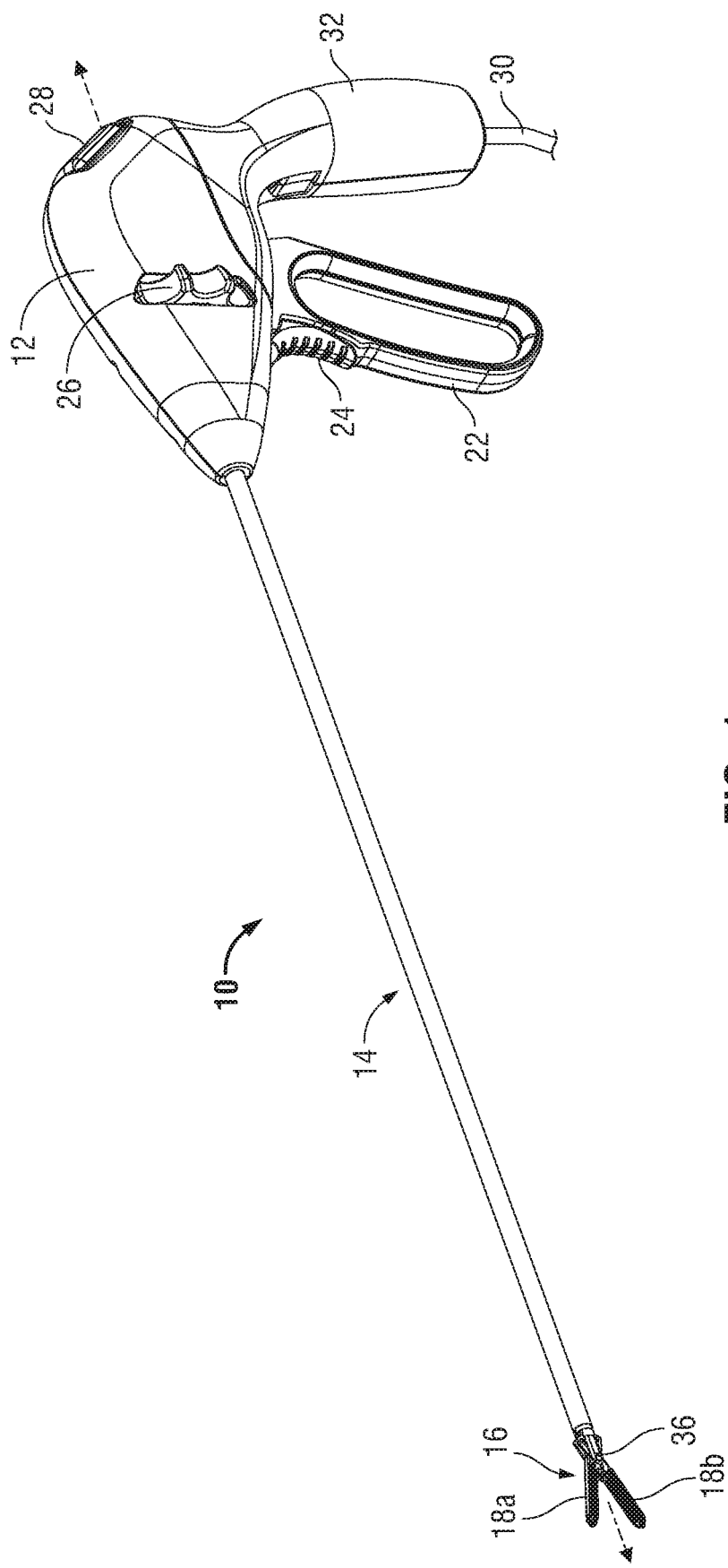
FIG. 1 is a perspective view of an endoscopic electrosurgical forceps configured for use in accordance with the present disclosure.

Referring initially to FIG. 1, an endoscopic electrosurgical forceps configured for use in accordance with the present disclosure is shown generally identified by reference numeral 10. Forceps 10 generally includes a housing 12, an elongated shaft 14 extending distally from housing 12, an end effector assembly 16 disposed at a distal end portion of elongated shaft 14, a movable handle 22, a trigger 24, a rotation knob 26, an activation switch 28, and an electrosurgical cable 30. End effector assembly 16 includes first and second jaw members 18a, 18b, as detailed below.

Movable handle 22 is operably coupled to housing 12 and movable relative to a stationary handle portion 32 of housing 12 between an initial position and a compressed position. A drive assembly (not shown) extends through housing 12 and elongated shaft 14 and is operably coupled between movable handle 22 and first and second jaw members 18a, 18b of end effector assembly 16 such that movement of movable handle 22 between the initial position and the compressed position pivots one or both of jaw members 18a, 18b relative to the other between a spaced-apart position (FIG. 2A) and an approximated position (FIG. 2B). A suitable drive assembly for these purposes is detailed in U.S. Patent Application Pub. No. 2013/0296922 to Allen, I V et al., the entire contents of which are hereby incorporated herein by reference.

Trigger 24 is operably coupled to housing 12 and movable relative thereto between an un-actuated position and an actuated position. A knife deployment assembly (not shown) extends through housing 12 and elongated shaft 14 and is operably coupled between trigger 24 and a knife 34 (FIG. 2A) associated with end effector assembly 16 such that movement of trigger 24 from the un-actuated position to the actuated position advances knife 34 from a retracted position to an extended position, wherein knife 34 extends between jaw members 18a, 18b (see FIG. 2A). A knife deployment assembly for these purposes is detailed in U.S. Patent Application Pub. No. 2013/0296922 to Allen, I V et al., previously incorporated herein by reference in its entirety.

Rotation knob 26 is operably associated with housing 12 and extends from either side thereof to enable manual manipulation by a user. Rotation knob 26 is coupled to elongated shaft 14 which, in turn, supports end effector assembly 16 at a distal end portion thereof. As a result, rotation of rotation knob 26 in either direction rotates elongated shaft 14 and end effector assembly 16 relative to housing 12 in a corresponding direction.

Activation switch 28 is disposed on housing 12, while electrosurgical cable 30 extends from housing 12. Electrosurgical cable 30 is adapted to connect to a source of energy, e.g., an electrosurgical generator (not shown), and includes a plurality of electrical lead wires (not shown) extending therethrough and into housing 12. The electrical lead wires (not shown) are configured to electrically couple the electrosurgical generator with activation switch 28 and jaw members 18a, 18b of end effector assembly 16 such that electrosurgical energy is supplied to jaw members 18a, 18b upon activation of activation switch 28. As an alternative to electrosurgical cable 30 being adapted to connect to a remote electrosurgical generator, forceps 10 may be configured as a cordless, handheld instrument including power and energy-generation components disposed on or within housing 12.

Figure 2A:
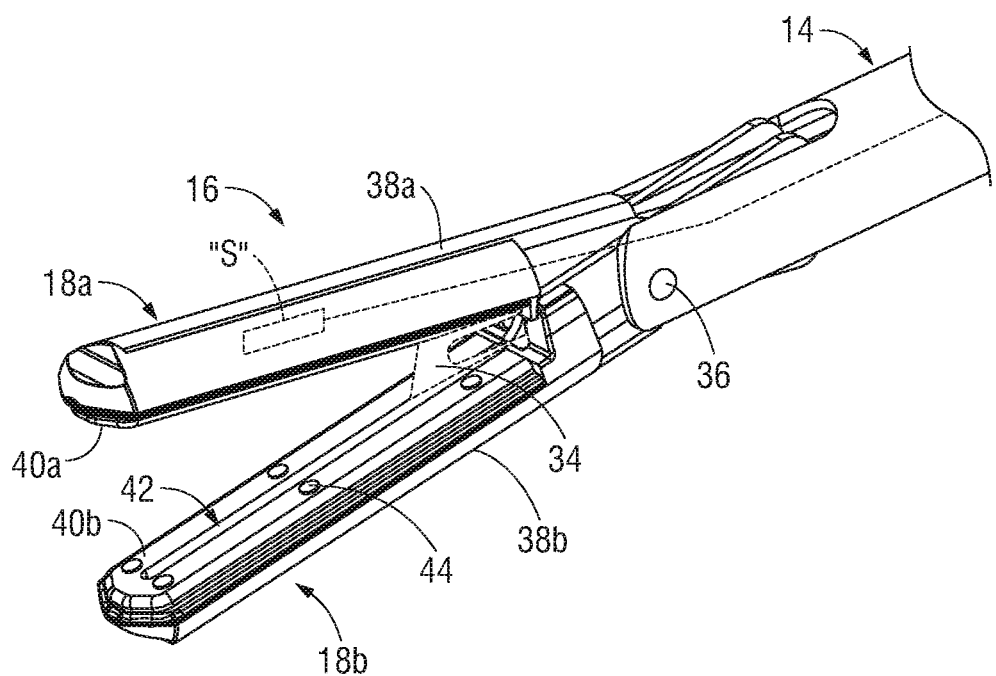
FIG. 2A is an enlarged, perspective view of an end effector assembly of the forceps of FIG. 1 with jaw members thereof disposed in a spaced-apart position.
Figure 2B:
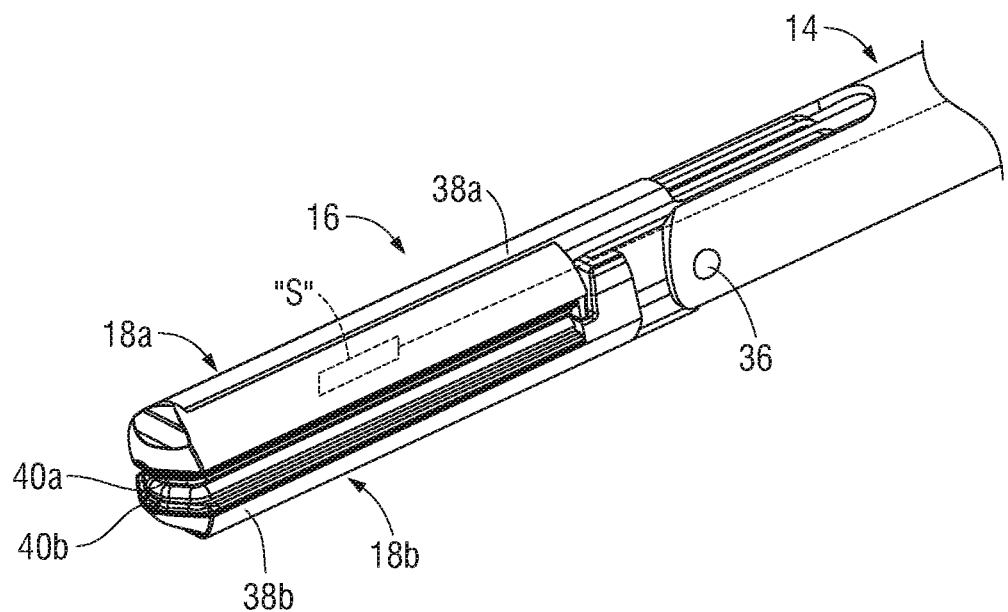
FIG. 2B is an enlarged, perspective view of the end effector assembly of FIG. 2A with the jaw members thereof disposed in an approximated position.

With reference to FIGS. 2A and 2B, as noted above, end effector assembly 16 is disposed at a distal end portion of elongated shaft 14 and includes first and second jaw members 18a, 18b. One or both of jaw members 18a, 18b is pivotable relative to the other and elongated shaft 14 about a pivot pin 36. For the purposes herein, "movement" or "pivoting" of the jaw members 18a, 18b refers to both bilateral configurations, e.g., wherein both jaw members 18a, 18b pivot relative to elongated shaft 14, and unilateral configurations, e.g., wherein one jaw member 18a, 18b is fixed relative to elongated shaft 14 and the other jaw member 18a, 18b is pivotable relative to the fixed jaw member 18a, 18b and elongated shaft 14. Each jaw member 18a, 18b includes an outer insulative housing 38a, 38b, an electrically-conductive tissue-contacting surface 40a, 40b supported on the respective outer insulative housing 38a, 38b, and a longitudinally-extending knife channel 42 (only knife channel 42 of jaw member 18b is shown) defined within the respective tissue-contacting surface 40a, 40b. One or both of jaw members 18a, 18b may further include one or more stop members 44 operably associated with, e.g., disposed on, the tissue-contacting surface 40a, 40b thereof for maintaining a minimum separation distance between tissue-contacting surfaces 40a, 40b in the approximated position of jaw members 18a, 18b.

With jaw members 18a, 18b disposed in the approximated position grasping tissue therebetween, electrosurgical energy may be delivered from the generator (not shown) to tissue-contacting surfaces 40a, 40b via electrosurgical cable 30 upon activation of activation switch 28. Tissue-contacting surfaces 40a, 40b are configured, upon energization, to conduct energy through tissue grasped therebetween to treat tissue. Once tissue is treated, or where it is only desired to grasp and cut tissue, trigger 24 (FIG. 1) is actuated to advance knife 34 through longitudinally-extending knife channels 42 of jaw members 18a, 18b to cut tissue grasped therebetween. In some embodiments, a knife lockout (not shown) is provided to inhibit actuation of knife 34 when jaw members 18a, 18b are disposed in the spaced-apart position.

Figure 3:
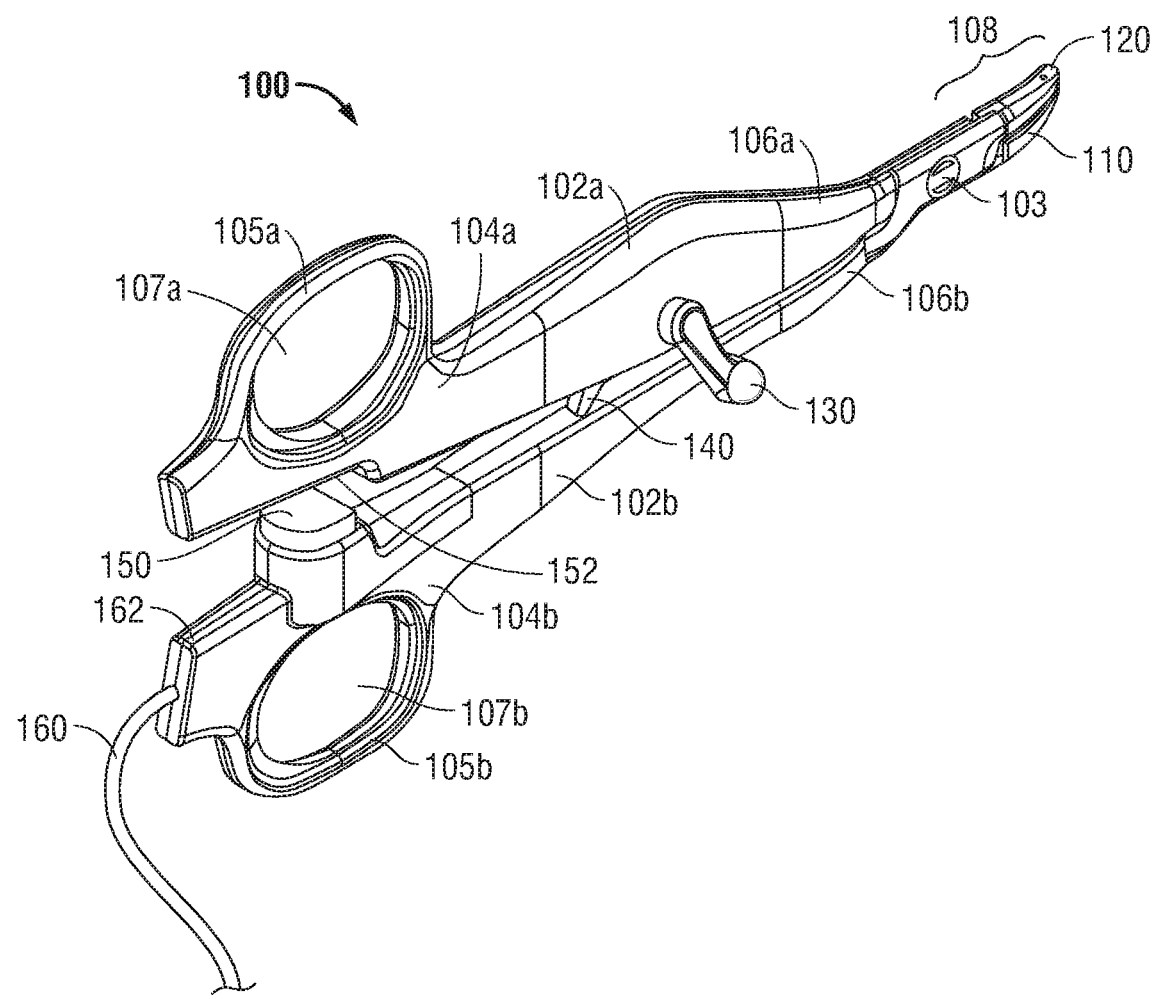
FIG. 3 is a perspective view of an open electrosurgical forceps configured for use in accordance with the present disclosure.

Turning to FIG. 3, an open electrosurgical forceps configured for use in accordance with the present disclosure is shown generally identified by reference numeral 100. Forceps 100 includes first and second elongated shafts 102a, 102b each having a proximal end portion 104a, 104b and a distal end portion 106a, 106b, respectively. An end effector assembly 108 of forceps 100 includes first and second jaw members 110, 120 attached to the distal end portions 106a, 106b of elongated shafts 102a, 102b, respectively. Elongated shafts 102a, 102b are pivotably coupled to one another about a pivot 103 such that elongated shafts 102a, 102b are movable relative to one another between an open position and a closed position to thereby move first and second jaw members 110, 120 about pivot 103 and relative to one another from a spaced-apart position to an approximated position.

Each elongated shaft 102a, 102b include a handle 105a, 105b disposed at the proximal end portion 104a, 104b thereof. Each handle 105a, 105b defines a finger hole 107a, 107b therethrough for receiving a finger of the user to facilitate movement of elongated shafts 102a, 102b between the open and closed positions.

One of the elongated shafts, e.g., elongated shaft 102a, is configured to house a knife (not shown; similar to knife 34 of forceps 10 (FIG. 2A)) and knife deployment assembly (not shown), and includes a trigger 130 disposed on either side thereof. The knife deployment assembly (not shown) extends through elongated shaft 102a and is operably coupled between triggers 130 and knife 34 such that movement of either of triggers 130 from an un-actuated position to an actuated position advances knife 34 from a retracted position to an extended position, wherein knife 34 extends between jaw members 110, 120. A knife deployment assembly for these purposes is detailed in U.S. Patent Application Pub. No. 2012/0083786 to Artale et al., the entire contents of which are hereby incorporated herein by reference. Forceps 100 may further include a knife lockout 140 to inhibit actuation of knife 34 when elongated shafts 102a, 102b are disposed in the open position corresponding to the spaced-apart position of jaw members 110, 120. Any suitable knife lockout may be provided, such as any one of the embodiments of knife lockouts disclosed in U.S. Patent Application Pub. No. 2012/0083827 to Artale et al., the entire contents of which are hereby incorporated herein by reference.

Continuing with reference to FIG. 3, elongated shaft 102b includes an activation switch 150 disposed thereon at the proximal end portion 104b thereof. Activation switch 150 aligns with an opposing surface 152 of the proximal end portion 104a of elongated shaft 102a such that upon movement of elongated shafts 102a, 102b to the closed position, activation switch 150 is urged to an activated position via opposing surface 152 of elongated shaft 102a. An electrosurgical cable 160 extends from a proximal shaft connector 162 of elongated shaft 102b. Electrosurgical cable 160 is adapted to connect to a source of energy, e.g., an electrosurgical generator (not shown), and includes a plurality of electrical lead wires (not shown) extending therethrough and into elongated shaft 102b. The electrical lead wires (not shown) are configured to electrically couple the electrosurgical generator with activation switch 150 and jaw members 110, 120 of end effector assembly 108 such that electrosurgical energy is supplied to jaw members 110, 120 upon activation of activation switch 150.

Jaw members 110, 120 of end effector assembly 108 of forceps 100 are similar to and may include any of the features of jaw members 18a, 18b of end effector assembly 16 of forceps 10 (FIGS. 1-2B). Accordingly, for purposes of brevity, jaw members 110, 120 are not detailed herein.

Figure 4:
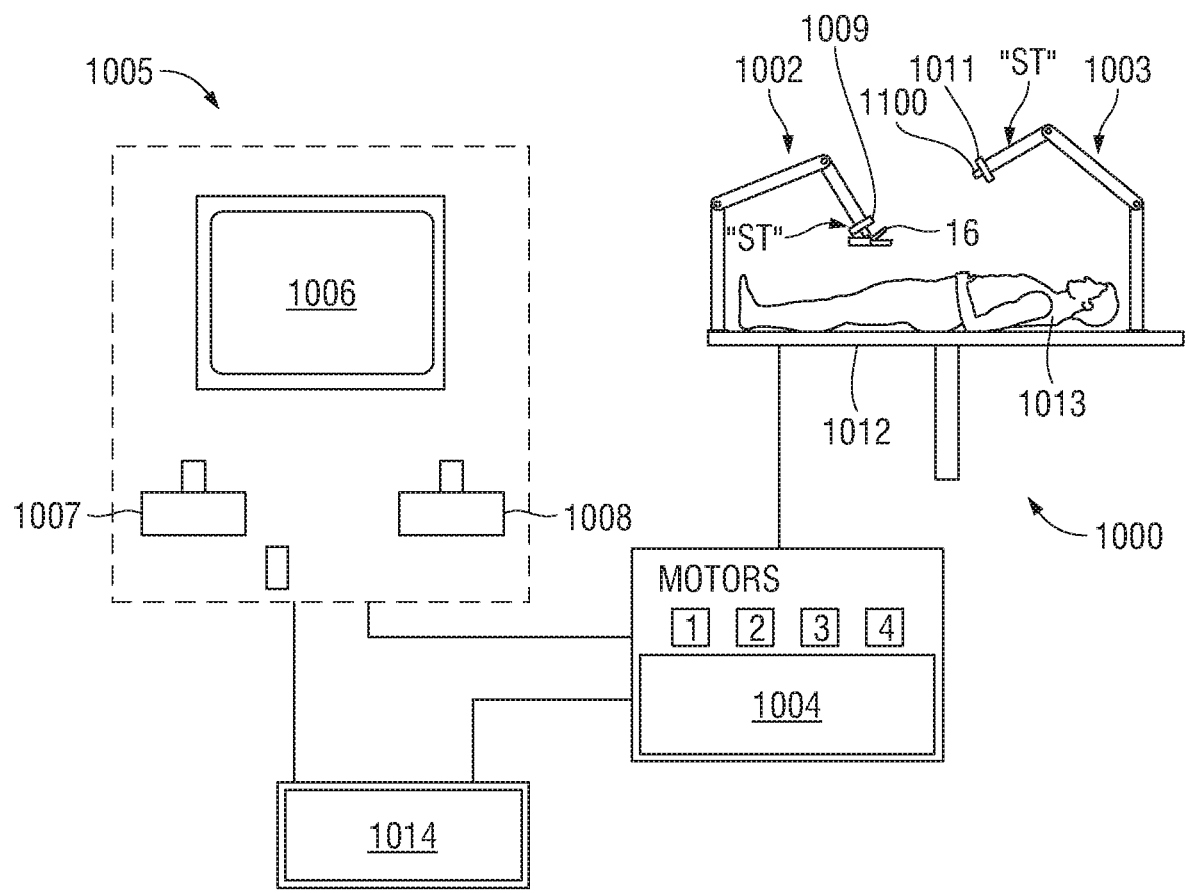
FIG. 4 is a schematic illustration of a robotic surgical system configured for use in accordance with the present disclosure.

Referring to FIG. 4, a robotic surgical system configured for use in accordance with the present disclosure is shown generally identified by reference numeral 1000. For the purposes herein, robotic surgical system 1000 is generally described. Aspects and features of robotic surgical system 1000 not germane to the understanding of the present disclosure are omitted to avoid obscuring the aspects and features of the present disclosure in unnecessary detail.

Robotic surgical system 1000 generally includes a plurality of robot arms 1002, 1003; a control device 1004; and an operating console 1005 coupled with control device 1004. Operating console 1005 may include a display device 1006, which may be set up in particular to display three-dimensional images; and manual input devices 1007, 1008, by means of which a person (not shown), for example a surgeon, may be able to telemanipulate robot arms 1002, 1003 in a first operating mode. Robotic surgical system 1000 may be configured for use on a patient 1013 lying on a patient table 1012 to be treated in a minimally invasive manner. Robotic surgical system 1000 may further include a database 1014, in particular coupled to control device 1004, in which are stored, for example, pre-operative data from patient 1013 and/or anatomical atlases.

Each of the robot arms 1002, 1003 may include a plurality of members, which are connected through joints, and an attaching device 1009, 1011, to which may be attached, for example, a surgical tool "ST" supporting an end effector assembly 16, 1100. End effector assembly 16 may be the end effector assembly of endoscopic surgical forceps 10 (FIG. 1), detailed above, or any other suitable end effector assembly. With respect to embodiments where one of the surgical tools "ST" is end effector assembly 16, robotic surgical system 1000 functions as an electrosurgical forceps configured to manipulate and/or actuate end effector assembly 16 so as to enabling the grasping, treating, and dividing of tissue, similarly as detailed above with respect to forceps 10 (FIG. 1). End effector assembly 1100 may be any other suitable surgical end effector, e.g., an endoscopic camera, other surgical tool, etc. Robot arms 1002, 1003 may be driven by electric drives, e.g., motors, connected to control device 1004. Control device 1004, e.g., a computer, may be configured to activate the motors, in particular by means of a computer program, in such a way that robot arms 1002, 1003, their attaching devices 1009, 1011, and, thus, the surgical tools "ST" (including end effector assemblies 16, 1100) execute a desired movement and/or function according to a corresponding input from manual input devices 1007, 1008, respectively. Control device 1004 may also be configured in such a way that it regulates the movement of robot arms 1002, 1003 and/or of the motors.

Endoscopic electrosurgical forceps 10 (FIG. 1), open electrosurgical forceps 100 (FIG. 3), and robotic surgical system 1000 (FIG. 4) each include end effector assemblies capable of grasping tissue, treating tissue with electrosurgical energy, and dividing tissue. Provided in accordance with the present disclosure, and detailed below with reference to FIGS. 5-8B, is an adapter 500 configured for use with electrosurgical forceps 10 (FIG. 1), open electrosurgical forceps 100 (FIG. 3), robotic surgical system 1000 (FIG. 4), and/or any other suitable surgical instrument for providing such with clip-applying functionality. Thus, although adapter 500 is detailed below in use connection with end effector 16 of forceps 10, it is understood that adapter 500 is equally applicable for use with any suitable surgical instrument to provide such with clip-applying functionality.

Referring to FIGS. 5-8B, adapter 500 includes a pair of jaws bodies 510 coupled to one another via an interconnect band 530. Adapter 500 may be monolithically formed as an integral component e.g., via injection molding, extrusion, etc., and may be constructed from plastic, although adapter 500 may alternatively define any other suitable configuration and/or be formed via any other suitable material(s) and/or manufacturing process(es). As detailed below, adapter 500 is configured to receive a surgical clip 600 therebetween and, in cooperation with end effector assembly 16, form surgical clip 600 about tissue. Although one embodiment of a surgical clip 600 is detailed herein, adapter 500 may additionally or alternatively be configured for use with other surgical clips of varying size and/or configuration.

Jaw bodies 510 define substantially similar configurations and, thus, are collectively referred to hereinbelow in the singular. However, in some embodiments, the jaw bodies 510 may define different configurations, e.g., where adapter 500 is configured for use with a surgical clip having asymmetric legs.

Jaw body 510 includes a support plate 512 defining a proximal end portion 514 and a distal end portion 516, a chuck 518 disposed on an inwardly-facing side of support plate 512 towards the distal end portion 516 thereof, and an elongated fin 520 disposed on an outwardly-facing side of support plate 512 and extending from proximal end portion 514 thereof longitudinally along support plate 512. Support plate 512 defines an inwardly-facing surface 513a, from which chuck 518 extends, and an outwardly-facing surface 513b, from which elongated fin 520 extends. The exposed portion of outwardly-facing surfaces 513b, e.g., the portions surrounding elongated fin 520, are configured to sit atop the tissue-contacting surfaces 40a, 40b of the corresponding jaw member 18a, 18b of end effector assembly 16 when adapter 500 is engaged with end effector assembly 16.

Chuck 518, as noted above, is disposed on the inwardly-facing side of support plate 512 towards distal end portion 516 thereof. Chuck 518 may extend over about half (e.g., 40% to 60%) of the length of support plate 512, although other configurations are also contemplated. Thus, a proximal half of inwardly-facing surface 513a of support plate 512 is exposed. Chuck 518 defines a longitudinally-extending channel 519a defined therethrough that is configured to receive a portion of a leg 610 of surgical clip 600 therein. Chuck 518 further includes a pair of spaced-apart feet 519b extending distally from support plate 512. Each foot 519b defines a semi-circular recess 519c, each of which is configured to receive a location knob 616 of one of the legs 610 of surgical clip 600 to facilitate proper alignment and retention of the leg 610 of the surgical clip 600 within channel 519a, as detailed below.

Elongated fin 520, as noted above, is disposed on an outwardly-facing side of support plate 512 and extends distally from proximal end portion 514 thereof. However, as longitudinally-extending knife channels 42 of jaw members 18a, 18b of end effector assembly 16 do not extend all the way to the distal ends of jaw members 18a, 18b, elongated fin 520 does not extend all the way to the distal end of support plate 512. Further, elongated fin 520 defines a height profile that compliments a depth profile of the knife channel 42 of the corresponding jaw member 18a, 18b of end effector assembly 16 to enable receipt of elongated fin 520 therein. Elongated fin 520 further defines a width that generally approximates the width of the corresponding knife channel 42 to minimize play therebetween. In some embodiment, elongated fin 520 may be configured for friction-fit engagement within the corresponding knife channel 42.

Alternatively, retention of the jaw bodies 510 in engagement with the corresponding jaw members 18a, 18b may be maintained by way of interconnect band 530, as detailed below.

Interconnect band 530 defines an arcuate configuration and extends proximally from proximal end portion 514 of support plate 512 of each jaw body 510. In an initial at-rest position of adapter 500, interconnect band 530 defines a first radius of curvature. In response to urging of either or both of jaw bodies 510 towards the other, interconnect band 530 is configured to flex such that adapter 500 is moved from the at-rest position to a flexed position, wherein jaw bodies 510 are disposed in closer approximation relative to one another and interconnect band 530 defines a second, reduced radius of curvature. Interconnect band 530 may be resiliently flexible such that, upon removal of forces thereon, interconnect band 530 returns adapter 500 to the at-rest position, thus enabling multiple uses for applying a plurality of surgical clips 600, or may be partially-resilient such that interconnect band 530 returns adapter 500 to an intermediate position upon removal of forces thereon to enable adapter 500 to be withdrawn from about surgical clip 600 without returning adapter 500 to the at-rest position. In such partially-resilient configurations, adapter 500 may be configured for single-use.

In the at-rest position of adapter 500, interconnect band 530, as noted above, defines a first radius of curvature. This first radius of curvature may correspond to an angle between jaw bodies 510 that is greater than an angle between jaw members 18a, 18b of end effector assembly 16 in a furthest spaced-apart position of jaw members 18a, 18b. As such, interconnect band 530 is required to be flexed towards the flexed position of adapter 500 upon insertion of adapter 500 between jaw members 18a, 18b. Thus, with adapter 500 installed between jaw members 18a, 18b and jaw members 18a, 18b disposed in the furthest spaced-apart position, adapter 500 is disposed in a pre-compressed condition. As a result, jaw bodies 510 are urged towards the corresponding jaw members 18a, 18b, thus retaining each jaw body 510 in operable engagement with the corresponding jaw member 18a, 18b.

In order to operably engage adapter 500 with end effector assembly 16, jaw members 18a, 18b are first moved to, or confirmed to be in, the further spaced-apart position thereof. Adapter 500, lead by interconnect band 530, is then translated proximally between jaw members 18a, 18b with fins 520 aligned with knife channels 42. As adapter 500 is translated proximally, due to the angle between jaw bodies 510 in the at-rest position of adapter 500 being greater than the angle between jaw members 18a, 18b in the furthest spaced-apart position of jaw members 18a, 18b, jaw bodies 510 of adapter 500 are eventually urged towards one another beyond the pre-compressed condition of adapter 500. Once fins 520 clear the distal end portions of tissue-contacting surface 40a, 40b of jaw members 18a, 18b and are aligned with knife channels 42 along the entire lengths of fins 520, jaw bodies 510 are resiliently returned towards the initial position of adapter 500 under the bias of interconnect band 530. This bias of jaw bodies 510 towards the at-rest position of adapter 500 urges fins 520 into knife channels 42 until outwardly-facing surfaces 513b of support plates 514 of jaw bodies 510 abut tissue-contacting surfaces 40a, 40b of jaw members 18a, 18b. As noted above, adapter 500 is not returned to the at-rest position when operably engaged with end effector assembly 16 but, rather, is retained therein in a pre-compressed condition, thus facilitating retention of adapter 500 in operable engagement with end effector assembly 16. Surgical clip 600 may be installed on adapter 500 prior to or subsequent of adapter 500 being operably engaged with end effector assembly 16.

Continuing with reference to FIGS. 5-8B, surgical clip 600 includes a pair of legs 610 interconnected by a backspan 620. Surgical clip 600 may be monolithically formed as a single component from a suitable metal, plastic, or other suitable material, or may be a multi-component clip. Although one configuration of a surgical clip 600 is detailed herein, other suitable surgical clips may also be provided such as, for example, the surgical clips detailed in U.S. Pat. Nos. 4,834,096; 7,819,886; and 7,905,890, the entire content of each of which is hereby incorporated herein by reference.

Each leg 610 of surgical clip 600 defines a generally rectangular cross-sectional configuration, although other configurations may alternatively be provided, and has a width that generally approximates the width of the channel 519a of the chuck 518 of the corresponding jaw body 510 of adapter such that a portion of each leg 610 is receivable within the corresponding channel 519a. Each leg 610 further defines a fixed proximal end portion 612 and a free distal end portion 614. A location knob 616 extends transversely from either side of each leg 610 at the distal end portion 614 thereof. Location knobs 616 are configured for receipt within recesses 519c of feet 519b of chucks 518 of the corresponding jaw bodies 510 so as to retain surgical clip 600 in operable engagement with and proper orientation relative to adapter 500. Legs 610 may further include a series of complementary grooves 618a and ribs 618b disposed on inwardly-facing surfaces thereof and configured to mate with one another in the formed position of surgical clip 600, thus facilitating alignment of legs 610 in the formed position of surgical clip 600.

Backspan 620 of surgical clip 600 extends proximally from and interconnects proximal end portions 612 of legs 610. Backspan 620 defines an arcuate configuration and is deformable from an initial condition of surgical clip 600, wherein backspan 620 defines a first radius of curvature, to a formed condition of surgical clip 600, wherein backspan 620 defines a second radius of curvature less than the first radius of curvature. In the initial condition of surgical clip 600, backspan 620 exhibits resiliency through an initial range of motion such that, backspan 620 biases surgical clip 600 towards the initial condition upon urging of legs 610 towards one another within the initial range of motion. However, backspan 620 is permanently deformable once the initial range of motion has been exceeded such that surgical clip 600 is maintained in the formed condition after reaching the formed condition. The initial resilience of backspan 620 enables surgical clip 600 to be pre-compressed upon positioning within adapter 500 to retain surgical clip 600 therein, similarly as detailed above with respect to adapter 500 and jaw members 18a, 18b. As an alternative to permanent deformation, backspan 620 may exhibit resiliency through the entire range of motion of legs 610. In such configurations, legs 610 may include mechanical engagement features (not shown) at the distal ends portions 614 thereof to mechanically lock surgical clip 600 in the formed condition upon achieving the formed condition.

In order to engage surgical clip 600 with adapter 500, surgical clip 600, lead by backspan 620 is translated proximally between jaw bodies 510 of adapter 500 with legs 610 aligned with channels 519a of chucks 518 of jaw bodies 510. As surgical clip 600 is translated proximally, or prior thereto, legs 610 of surgical clip 600 are moved towards one another to permit receipt of legs 610 of surgical clip 600 between jaw bodies 510 of adapter 500. Surgical clip 600 is translated proximally relative to adapter 500 until location knobs 616 of legs 610 of surgical clip 600 are aligned with respective recesses 519c of jaw bodies 510 of adapter 500. Once this alignment has been achieved, surgical clip 600 may be released to return towards the initial condition. This bias of legs 610 towards the initial condition of surgical clip 600 urges legs 610 into channels 519a and urges location knobs 616 into recesses 519c. As noted above, surgical clip 600 is not returned to the initial condition when engaged with adapter 500 but, rather, is retained therein in a pre-compressed condition, thus facilitating retention of surgical clip 600 in engagement with adapter 500 prior to formation thereof.

With general reference to FIGS. 1-2B forceps 10, as noted above, may be used to grasp tissue between tissue-contacting surfaces 40a, 40b, apply electrosurgical energy to the grasped tissue to treat tissue, and/or divide the grasped tissue. With additional reference to FIGS. 5-8B, where, during the course of a surgical procedure, it is necessary to apply a surgical clip 600, adapter 500 may be operably engaged with end effector assembly 16, as detailed above. As also noted above, surgical clip 600 may be loaded into adapter 500 prior to or subsequent of operable engagement of adapter 500 with end effector assembly 16.

With adapter 500 and surgical clip 600 operably engaged with one another and end effector assembly 16, forceps 10 may be utilized to form surgical clip 600 about tissue. In order to form surgical clip 600 about tissue, movable handle 22 is moved relative to stationary handle portion 32 of housing 12 from the initial position towards the compressed position such that the drive assembly (not shown) urges jaw members 18a, 18b of end effector assembly 16 to pivot from the spaced-apart position (FIGS. 2A and 7) towards and the approximated position (FIG. 2B). As jaw members 18a, 18b are urged towards the approximated position, tissue-contacting surfaces 40a, 40b of jaw members 18a, 18b urge support plates 512 of jaw bodies 510 of adapter 500 towards one another, thereby urging adapter 500 towards the flexed position. Urging of adapter 500 towards the flexed position, in turn, urges legs 610 of surgical clip 600 towards one another to the formed condition of surgical clip 600. Movable handle 22 is moved sufficiently towards the compressed position to achieve the fully-flexed position of adapter 500 corresponding to the fully-formed condition of surgical clip 600, wherein legs 610 of surgical clip terminate the flow of fluid through the tissue about which surgical clip 600 formed.

Once surgical clip 600 is moved to the deformed condition (see FIGS. 8A and 8B) to terminate the flow of fluid through the tissue, jaw members 18a, 18b may be returned to the spaced-apart position, e.g., via release or return of movable handle 22, and, thereafter, end effector assembly 16 and adapter 500 may be removed, leaving behind surgical clip 600. Further application of surgical clips 600 using adapter 500 and end effector assembly 16 and/or further grasping, treating, and dividing of tissue using end effector assembly 16 may then be effectuated, depending upon the particular procedure to be performed.

In some embodiments, after formation of surgical clip 600 about tissue, tissue-contacting surfaces 40a, 40b may be energized to treat tissue surrounding surgical clip 600, e.g., via activation of activation switch 28 (FIG. 1). In some embodiments, one or more sensors "S" (FIGS. 2A and 2B), e.g., mechanical switches, electrical sensors, optical sensors, etc., disposed within either or both of jaw members 18a, 18b may be provided to sense engagement of adapter 500 with end effector assembly 16. Such sensors "S" may further be configured to communicate with activation switch 28 (FIG. 1) and/or the electrosurgical generator to inhibit the supply of energy to tissue-contacting surfaces 40a, 40b when adapter 500 is engaged therein, or to signal the electrosurgical generator to supply a suitable energy for use in treating tissue surrounding surgical clip 600 upon activation of activation switch 28 (FIG. 1).

Figure 5:
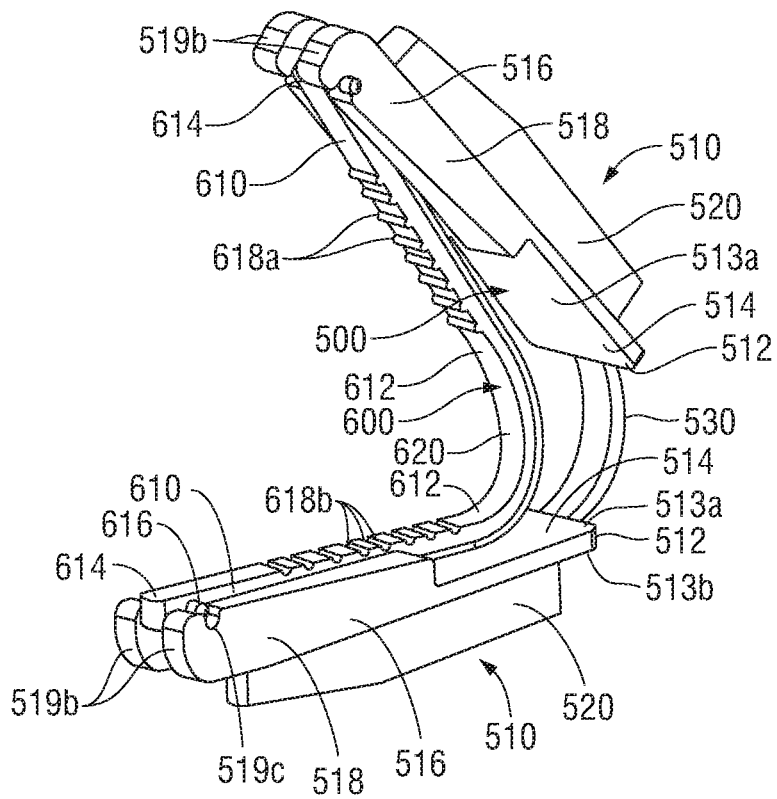
FIG. 5 is a perspective view of an adapter provided in accordance with the present disclosure including a surgical clip engaged therein.
Figure 6:
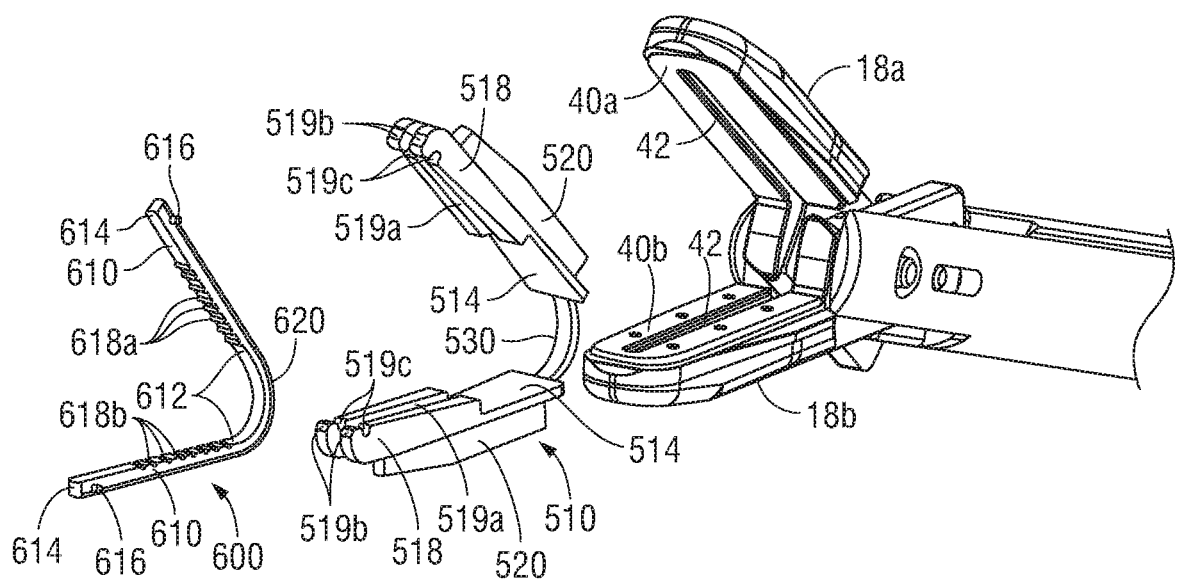
FIG. 6 is an exploded, perspective view illustrating coupling of the surgical clip of FIG. 5 with the adapter of FIG. 5 and the engagement thereof with the end effector assembly of the forceps of FIG. 1.
Figure 7:
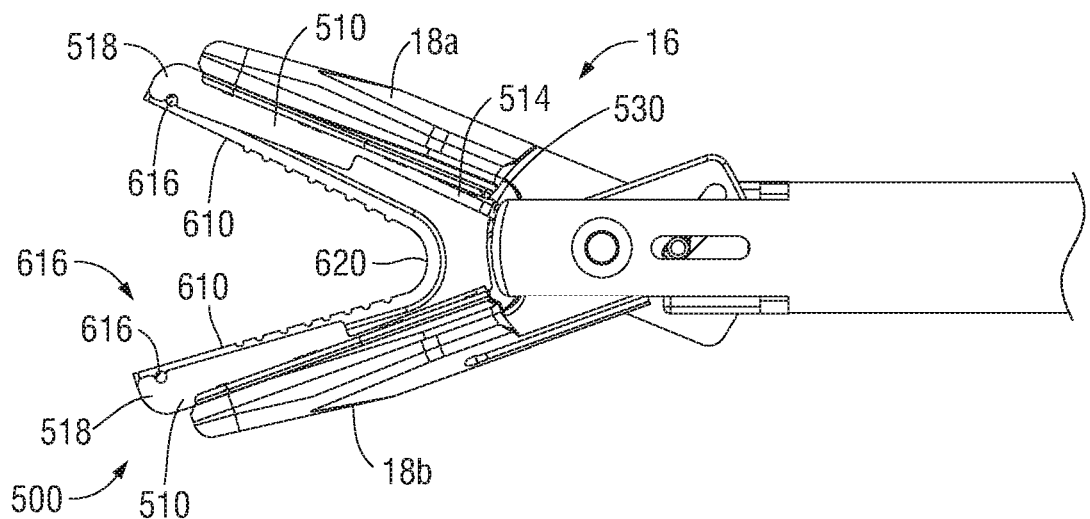
FIG. 7 is a side view illustrating engagement of the surgical clip and adapter of FIG. 5 with the end effector assembly of the forceps of FIG. 1, wherein the jaw members of the end effector assembly are disposed in the spaced-apart position.
Figure 8A:
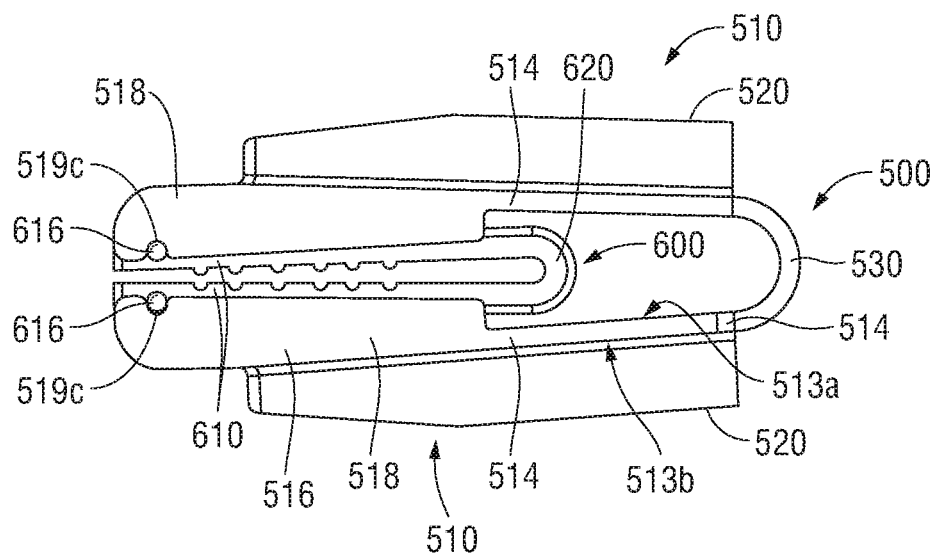
FIG. 8A is a side view of the adapter and surgical clip of FIG. 5, wherein the adapter is disposed in a closed condition corresponding to a formed condition of the surgical clip.
Figure 8B:
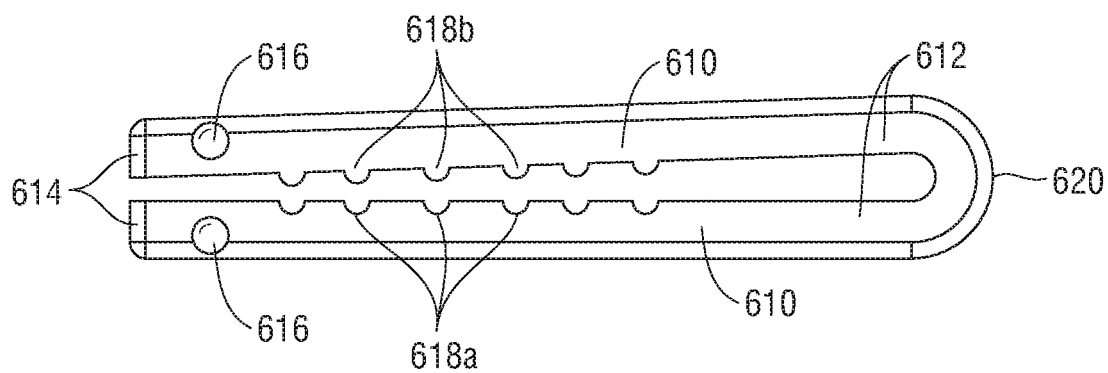
FIG. 8B is a side view of the surgical clip of FIG. 5 in the formed condition.

With reference to FIGS. 4 and 5, in embodiments where robotic surgical system 1000 is utilized, end effector assembly 1100 may be configured to retain an adapter 500 and one or more surgical clips 600 to enable automatic loading of adapter 500 and a surgical clip 600 within end effector assembly 16 and to enable automatic replacement of the surgical clip 600 with a second surgical clip 600 after formation of the first surgical clip 600.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as examples of particular embodiments. Those skilled in the art will envision other modifications within the scope and spirit of the claims appended hereto.

Although the foregoing disclosure has been described in some detail by way of illustration and example, for purposes of clarity or understanding, it will be obvious that certain changes and modifications may be practiced within the scope of the appended claims.

What is claimed is:
1. A surgical system, comprising:
   a surgical forceps including an end effector assembly including a pair of jaw members each defining a tissue-contacting surface, the jaw members movable from a spaced-apart position to an approximated position;
   an adapter releasably engagable with the end effector assembly, the adapter including a pair of jaw bodies and an interconnect band coupling the jaw bodies with one another, each jaw body including a support plate configured for positioning on the tissue-contacting surface of one of the jaw members, and a chuck;
   a knife selectively translatable relative to the jaw members between a retracted position and an extended position, wherein the knife extends at least partially through a knife channel defined within and extending longitudinally through at least one of the tissue-contacting surfaces, and wherein the at least one of the jaw bodies of the adapter includes a fin configured for receipt within the knife channel of one of the jaw members; and
   a surgical clip releasably engagable with the adapter, the surgical clip including a pair of legs and a backspan interconnecting the legs, each leg configured for receipt at least partially within the chuck of one of the jaw bodies of the adapter,
   wherein, with the surgical clip engaged with the adapter and the adapter engaged with the end effector assembly, the jaw members are configured to move from the spaced-apart position towards the approximated position to move the jaw bodies towards one another to, in turn, urge the legs of the surgical clip towards one another to form the surgical clip.
2. The surgical system according to claim 1, wherein the tissue contacting surface of at least one of the jaw members is adapted to connect to a source of electrosurgical energy.

3. The surgical system according to claim 1, wherein the chuck of each jaw body defines a channel configured to receive a portion of one of the legs of the surgical clip therein.

4. The surgical system according to claim 1, wherein the chuck of each jaw body defines at least one location feature, and wherein each leg of the surgical clip defines at least one complementary location feature configured to engage the at least one location feature to facilitate alignment of the surgical clip relative to the adapter.

5. The surgical system according to claim 4, wherein the at least one location feature is at least one recess and wherein the at least one complementary location feature is at least one knob configured for engagement within the at least one recess.

6. The surgical system according to claim 4, wherein the chuck of each jaw body includes a pair of spaced-apart feet configured to receive a portion of the surgical clip therebetween, each foot defining one of the at least one location features.

7. The surgical system according to claim 1, wherein the adapter is engaged in a pre-compressed position within the end effector assembly.

8. The surgical system according to claim 7, wherein the adapter defines an at-rest position wherein the interconnect band defines a first radius of curvature, and wherein, when the adapter is engaged with the end effector assembly, the adapter is retained in the pre-compressed position wherein the interconnect band is flexed to define a second radius of curvature smaller than the first radius of curvature.

9. The surgical system according to claim 1, wherein the surgical clip is engaged in a pre-compressed position within the adapter.

10. The surgical system according to claim 9, wherein the surgical clip defines an initial condition wherein the backspan defines a first radius of curvature, and wherein, when the surgical clip is engaged with the adapter, the surgical clip is retained in the pre-compressed condition wherein the backspan is flexed to define a second radius of curvature smaller than the first radius of curvature.

\* \* \* \* \*